United States Patent [19]

Platt

[11] Patent Number: 5,496,812

[45] Date of Patent: Mar. 5, 1996

[54] TOPICAL PREPARATION OF TOLNAFTATE AND HYDROCORTISONE TO TREAT FUNGAL INFECTIONS OF THE SKIN

[76] Inventor: Chris E. Platt, 14352 Riviera St., Huntington Beach, Calif. 92647

[21] Appl. No.: 319,808

[22] Filed: Oct. 7, 1994

Related U.S. Application Data

[63] Continuation-in-part of Ser. No. 235,282, Apr. 29, 1994, abandoned.

[51] Int. Cl.[6] .......................... A61K 31/59; A61K 31/56; A61K 31/16; A61K 31/10

[52] U.S. Cl. .......................... 514/171; 514/168; 514/599; 514/712; 514/886

[58] Field of Search .................... 514/712, 599, 514/168, 171, 886

[56] References Cited

U.S. PATENT DOCUMENTS 4,879,287  11/1989  Orr et al. ............................ 514/171

*Primary Examiner*—Theodore J. Criares
*Attorney, Agent, or Firm*—James G. O'Neill

[57] ABSTRACT

A topical preparation of between 1% and 3% hydrocortisone and 1.5% and 4.5% tolnaftate, by weight, in a 2:3 ratio used for treating a fungal infection of the skin. The specified ratio provides an accelerated and non-toxic treatment.

14 Claims, No Drawings

TOPICAL PREPARATION OF TOLNAFTATE AND HYDROCORTISONE TO TREAT FUNGAL INFECTIONS OF THE SKIN

This application is a continuation in part application for an earlier filed application, Ser. No. 08/235,282 filed on Apr. 29, 1994 now abandoned.

FIELD OF THE INVENTION

This invention relates generally to topical preparations for treating fungal disease and more particularly to a topical application consisting of a 2:3 ratio of anti-inflammatory hydrocortisone and antifungal tolnaftate, which not only avoids many of the toxic side effects of previous preparations, but also increases the effectiveness of the antifungal and thereby decreases both the spread of the fungal infection and the length of the treatment period.

BACKGROUND OF THE INVENTION

Invention and use of topical applications to treat common fungal diseases such as tinea pedis and tinea cruris, more commonly known as athlete's foot and jock itch, is known to the public. The active ingredient in these preparations is generally an anti-fungal agent such as miconazole, clotrimazole, grisefulvin or tolnaftate, although some preparations instead utilize an antibiotic, such as Nystatin (TM). In addition to these anti-fungal agents, some preparations also include an anti-inflammatory agent, such as a strong steroid. However, all of these prior anti-fungal preparations have several inherent problems or side effects that decrease their effectiveness.

Currently, the most widely used topical anti-fungal preparations are Tinactin (TM) and Micatin (TM). The anti-fungal agent used in Tinactin (TM) is tolnaftate, and the agent in Micatin (TM) is miconizole. According to a double-blind study comparing the superiority of a combination anti-fungal (clotrimazole/steroidal (betamethasone dipropionate)) product Cutis 30 (2):258 by M. Y. Wortzel, H1, since relatively few side effects are associated with these products, both are available over-the-counter, and therefore very popular. But despite their popularity, the use of such anti-fungal preparations have weaknesses. The main problem associated with these preparations is that they are unable to curb the redness and itchiness that are typically associated with the fungal infection. If the pain and itch of a lesion is not lessened, a patient is likely to scratch the infected area and spread the infection. Thus, when using these anti-fungal preparations the lesions often increase in size and spread to other areas via auto infection.

To remedy the problem of inflammation and auto infection, several anti-fungal applications are available that not only include an anti-fungal agent, but also an anti-inflammatory agent. U.S. Pat. Nos. 5,219,877 to Shah et al., 5,110,809 to Wang et al. and 5,310,545 to Eisen all indicate that a combination of an anti-fungal agent and a corticosteroid anti-inflammatory agent can effectively treat fungal infections and decrease the inflammation of the infected area. Commercial products available of this type include Lotrisone (TM) and Mycolog (TM). Lotrisone (TM) contains 1% of the anti-fungal agent clotrimazole and 0.05% of the anti-inflammatory agent betamethasone dipropionate. Mycolog (TM) employs Nystatin as its acting anti-fungal, and triamcinalone as its anti-inflammatory agent. The introduction of these strong steroids into anti-fungal applications allows the anti-fungal agent to combat a fungal infection, while the steroid combats the inflammation and irritation caused by the infection.

However, these compounds have not been very successful because they have several inherent weaknesses which limit them to use only by prescription. First of all, the addition of anti-inflammatory steroids to skin preparations is not an obvious decision, as the steroid's molecular structure can cause the anti-fungal or antibiotic to become deactivated, and thus much less effective. In fact, steroids actually increase the spread of viral diseases. In addition, as W. F. Barkey points out in Striae and persistent tinea corporis related to prolonged use of betamethasome dipropionate 0.05% cream/clotrimazole 1% cream in the treatment of tinea cruris and tinea corporis in J AM Dermatol 1988;18:17:518-0, potent, concentrated forms of corticosteroids have several toxic side effects such as skin atrophy, rebound phenomenon and suppression of the adrenal cortex. Both nyastin and clotrimazole are also liver toxic. Therefore, while the addition of corticosteroids helps decrease fungal inflammation, it also decreases the effectiveness of the total preparation and creates other undesirable side effects.

To improve upon these preparations, the newest generation of antifungals are the allyl-amine non-steroidals such as Terbinafine and Naftifine. E. G. Evans et al. find in a comparison of tertinafine and clotrimazole in treating tinea pedis, Bmj 1993 (690):645–7 that these non-steroidal antifungal compounds work effectively and may also contain anti-inflammatory properties without using steroids. However, these compounds have also proven to have toxic side effects and are therefore only available with a physician's prescription and not widely used.

Thus there is a clear need for an anti-fungal preparation that can quickly combat a fungal infection, control inflammation and increase absoption without producing harmful side effects to the user. Thus, the new invention provides a combination of ingredients o that offers all of the advantages and none of the disadvantages of the prior art, thus allowing for improved treatment of common fungal infections. The present invention fulfills these needs and provides further related advantages.

SUMMARY OF THE INVENTION

The present invention is a topical preparation designed to effectively treat common fungal infections without causing severe side effects. The present invention utilizes hydrocortisone, a mild steroid, in combination with tolnaftate, a common, proven anti-fungal agent, in a 2:3 ratio. This formulation has been found, through a double-blind study, to have certain specific and desired advantages, most especially in the prescribed ratio.

The study referenced above is described in a paper entitled, "Pharmacological Test For Synergism Of Hydrocortisone And Tolnaftate", by Curtis D. Platt, the present inventor, and Chris Platt. This paper is hereby included into the present application by reference. The study describes results found in rats treated with the inventive preparation of the present application. It is noted that on page 6 of this paper, FIG. 7 shows two important considerations; one that the results of the use of these preparations is very sensitive to the ratio of HC to TN, and two, that the ratio of 2:3 is far superior to other ratios. This is a surprising result not previously known or published in the literature. Further, in FIGS. 1 to 3 on page 5 of this paper we find that the claimed ratio eliminates dermatitis far faster than the other ratios; up to 30–40 percent faster. The other results presented in this paper are equally compelling for drawing the conclusion that the claimed combination is a significant improvement over the state of the art for the intended purpose. In conclusion, we find that the combination of hydrocortisone and Tolnaftate is not identified in the prior art as a topical remedy for skin fungal infections, and more importantly the specific beneficial ratio of 2:3 of hydrocortisone to Tolnaftate is clearly shown to have synergistic benefits in both the magnitude of its beneficial results, and the shortened time necessary for complete healing.

At first glance, it appears that this combination does not constitute a new invention, as hydrocortisone is a widely accepted anti-inflammatory steroid, and the key ingredient in the commercial anti-inflammant Cortaid (TM) while tolnaftate is a well known antifungal, and the active ingredient in the commercially available athlete's foot remedy, Tinactin (TM). In addition, there is much prior art, including Lotrisone(TM), Mycolog(TM) and U.S. Pat. Nos. 5,219,877, 5,110,809 and 5,3 10,545, that utilizes an antifungal/steroid combination. In fact, U.S. Pat. No. 4,879,287 to Norman A. Orr and Michael J. Greenway, column 1, line 29 to column 2, line 38, specifically teaches the combination of hydrocortisone and antifungal agents, which could indeed include tolnaftate. Thus, it might be thought that it seems obvious to one of ordinary skill in the art at the time the inventions were made to use a tolnaftate and hydrocortisone combination to combat fungal infections.

However, a closer look at the literature reveals that none of the prior art teaches the specific formulation we have found to optimize the advantages of the tolnaftate/hydrocortisone combination. In fact, the methodology of the present invention embarks on an entirely different path than that of the prior art combinations. An examination of the prior art shows that steroids were introduced to antifungal preparations for the express purpose of reducing the inflammation of the infection. Thus, while prior art preparations utilize both antifungals and steroids, it employs them to act independently from one another, with both agents executing their particular functions as antifungals and anti-inflammants. However, the present invention teaches away from this co-existive yet independent usage of the two agents. Instead, the present invention employs both an antifungal and a mild steroid not only to perform their independent duties prescribed in the prior art, but also in an inventive formulation that allows then to act synergistically with each other to perform functions not taught or foreseen heretofore.

As detailed above, the stronger steroids used in much of the prior art tend to deactivate and thus decrease the effectiveness of the antifungal agent. U.S. Pat. No. 4,879,287 to Orr et al. prescribes the optional addition of an antifungal to a hydrocortisone solution to give the preparation an added anti-fungal benefit, but nowhere in the patent is the issue of absorption rate of the antifungal addressed. Thus, it would be expected that hydrocortisone, like other steroids, would decrease the effectiveness of the antifungal agent. However, the combination of hydrocortisone with tolnaftate in the proper 2:3 ratio teaches away from the prior art, and in fact introduces a compound in which the introduction of hydrocortisone actually greatly improves the absorption rate of tolnaftate.

This increased absorption rate is accomplished because of hydrocortisone's molecular structure, which consists of a large non-polar chain that can bind to the tolnaftate molecule and pull the combination through the large chain lipoproteins of the skin, deeply into the skin where fungal cells can hide. Thus, by using hydrocortisone in conjunction with tolnaftate, the preparation's absorption rate is increased from 3 $\mu g/cm^2$ to 5 $\mu g/cm^2$ a result that was not foreseen or predicted in any of the prior art.

Another synergistic effect of the proper hydrocortisone/tolnaftate mixture moves the present invention even further from the expectations of the prior art. While the prior art utilizes steroid/antifungal combinations strictly to reduce inflammations and fight fungi, in the present invention hydrocortisone and tolnaftate act synergistically, not only to reduce inflammation and increase absorption, but also to enhance and expedite the maturation of the fungus, thus greatly increasing the effectiveness of the antifungal and reducing the length of the treatment period.

The life cycle of fungi include a spore stage and a mycelia stage. In the spore stage the fungi is very resistant to environmental and chemical exposure and thus is unaffected by prior preparations. It is not until the fungi reach the mycelia stage that they can be effectively eradicated by tolnaftate or other antifungals. Therefore, prior steroid/antifungal compounds are often ineffective at completely treating an infection because some of the fungi are still in the spore stage at the time of treatment. However, an unexpected benefit of the hydrocortisone/tolnaftate compound is that it induces the fungi spores to more quickly advance into the mycelia stage, thereby allowing the preparation to more quickly combat the infection.

Thus, it is an object of the present invention to provide a topical preparation that quickly and effectively treats common fungal infections such as athlete's foot and jock itch. It is another object of the invention to incorporate hydrocortisone, a mild anti-inflammatory steroid, to reduce an infection's inflammation without resulting in any undesirable toxic side effects prevalent in prior preparations composed of more potent steroids. It is a further object of the present invention to improve upon all prior art by utilizing an antifungal and mild steroid that not only complete their independent functions, but also act synergistically to greatly improve the absorbency and expediency of the new preparation. It is another object of the invention to rapidly advance fungi spores into the mycelia stage where they can effectively be eradicated by the antifungal, and thereby decrease the length of the treatment period.

Other features and advantages of the present invention will become apparent from the following more detailed description, which illustrates, by way of example, the principles of the invention.

DETAILED DESCRIPTION OF THE PREFERRED EMBODIMENT

The present invention is a topical preparation designed to treat common fungal infections such as tinea cruris and tinea pedis, more commonly known as jock itch and athlete's foot. The acting agents of the preparation are hydrocortisone, a common, mild steroid, and tolnaftate, a common antifungal agent, and in a ratio of approximately 2 to 3 respectively.

When the preparation is created for use as a non-prescription, over-the-counter formulation, in accordance with FDA standards the preparation comprises 1% hydrocortisone and 1.5% tolnaftate by weight. However, if the invention is to be utilized as a prescribed preparation, then higher doses of each agent can be used so that, by weight, the preparation comprises between 1% and 3% hydrocortisone, and between 1.5% and 4.5% tolnaftate, in the discovered optimal ratio of approximately 2 to 3 respectively. A formulation of 3% hydrocortisone and 4.5% tolnaftate has been found to have maximal beneficial results for fungal infections of the skin.

Preferably, the vehicle system of this formulation is one of an emulsion or cream which is washable and easily removed. The vehicle system is preferably a simplified system in order to minimize component interactions, either physical or chemical, and to reduce cost. Preferably, the vehicle system is formed into a cream by the addition of emolienating agents. In this embodiment, the preparation includes an emollient of up to 50% by weight of the preparation, as a carrier of the hydrocortisone and tolnaftate. Preferable emolienating agents include polyoxyethylene (20) cety ether, methyl glucose ether (PPG-10-methyl glucose ether), glycerin, mineral oil and petrolatum.

The preparation also may include several other components, including water, alcohol, fragrance, a preservative and colorant. Water is employed up to 40% by weight of the preparation in order to establish a desired consistency and texture. Alcohol is used to bind the preparation, which includes between 10% and 80% alcohol by weight. In addition, the preparation includes up to 2% fragrance by weight to provide a desired scent to the preparation. The preparation also includes one preservative, such as salicylic acid, of up to 1.5% by weight of the preparation for maintaining shelf life. Finally, the preparation includes a coloring agent that establishes a pleasing and attractive color of the preparation.

While the invention has been described with reference to a preferred embodiment, it is to be clearly understood by those skilled in the art that the invention is not limited thereto. Rather, the scope of the invention is to be interpreted only in conjunction with the appended claims.

What is claimed is:

1. A preparation for the treatment of fungus infection comprising, by weight, between 1% and 3% hydrocortisone, and between 1.5% and 4.5% tolnaftate, in a ratio of approximately 2 to 3 respectively in said topical preparation.

2. The preparation of claim 1 further including an emollient of up to 50% by weight of the preparation, as a carrier of the hydrocortisone and tolnaftate, in the preparation.

3. The preparation of claim 2 further including water of up to 40% by weight of the preparation.

4. The preparation of claim 2 further including alcohol of between 10% and 80% by weight of the preparation.

5. The preparation of claim 2 further including a fragrance of up to 2% by weight of the preparation.

6. The preparation of claim 2 further including at least one preservative of up to 1.5% by weight of the preparation.

7. The preparation of claim 2 further including a coloring agent in the preparation.

8. A preparation for the treatment of fungus infection comprising, by weight, 1% hydrocortisone, and 1.5% tolnaftate, being in a ratio of 2 to 3 respectively in a nonprescription formulation as a topical preparation.

9. The preparation of claim 8 further including an emollient of up to 50% by weight of the preparation, as a carrier of the hydrocortisone and tolnaftate, in the preparation.

10. The preparation of claim 9 further including water of up to 40% by weight of the preparation.

11. The preparation of claim 9 further including alcohol of between 10% and 80% by weight of the preparation.

12. The preparation of claim 9 further including a fragrance of up to 2% by weight of the preparation.

13. The preparation of claim 9 further including at least one preservative of up to 1.5% by weight of the preparation.

14. The preparation of claim 9 further including a coloring, agent in the preparation.

* * * * *